United States Patent
Guala

(10) Patent No.: US 6,989,002 B2
(45) Date of Patent: Jan. 24, 2006

(54) FLAT FILTER FOR VENTING GAS IN INTRAVENOUS MEDICAL LINES

(75) Inventor: Gianni Guala, Turin (IT)

(73) Assignee: Industie Borla S.p.A., Moncalieri (IT)

( * ) Notice: Subject to any disclaimer, the term of this patent is extended or adjusted under 35 U.S.C. 154(b) by 0 days.

(21) Appl. No.: 10/687,692

(22) Filed: Oct. 20, 2003

(65) Prior Publication Data

US 2004/0138616 A1    Jul. 15, 2004

(30) Foreign Application Priority Data

Oct. 21, 2002  (IT)  .................. TO2002000912

(51) Int. Cl.
  *A61M 1/00* (2006.01)
  *A61M 5/00* (2006.01)
  *A61B 19/00* (2006.01)
(52) U.S. Cl. .................. 604/126; 604/252; 604/406
(58) Field of Classification Search ................ 604/122, 604/126, 190, 252, 406; 210/436
See application file for complete search history.

(56) References Cited

U.S. PATENT DOCUMENTS

| 4,326,957 A | * | 4/1982 | Rosenberg ................. 210/436 |
| 4,525,182 A | * | 6/1985 | Rising et al. .................... 96/6 |
| 6,347,711 B1 | | 2/2002 | Friederichs et al. | |

FOREIGN PATENT DOCUMENTS

| EP | 0 302 722 A2 | 2/1989 |
| EP | 0 784 988 A | 7/1997 |
| EP | 1 214 955 A | 6/2002 |

* cited by examiner

*Primary Examiner*—Michael J. Hayes
(74) *Attorney, Agent, or Firm*—Sughrue Mion, PLLC

(57) ABSTRACT

Flat filter for venting gas in intravenous medical lines, comprising a case formed by a frontal plate and by a dorsal plate between which a hydrophilic filtering membrane is interposed. The dorsal plate has a single through hole for gas venting in communication with an elongated collecting channel formed on the inner surface of the dorsal plate and along which a hydrophobic membrane of complementary shape is applied.

3 Claims, 3 Drawing Sheets

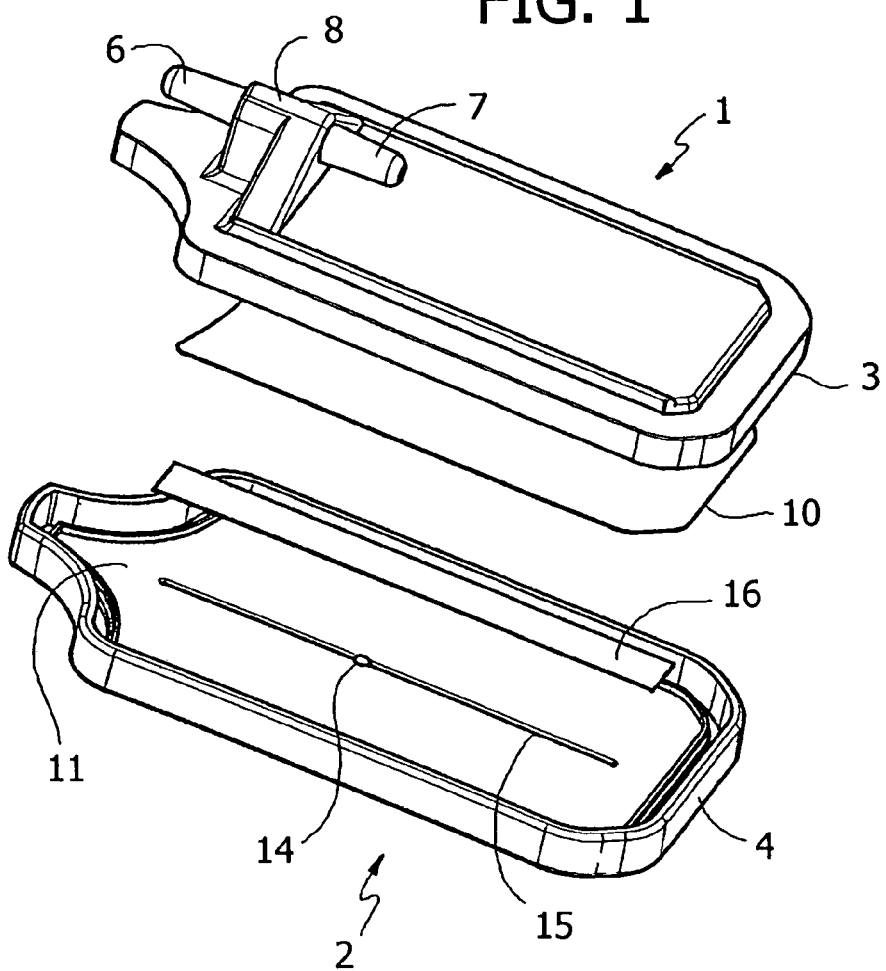
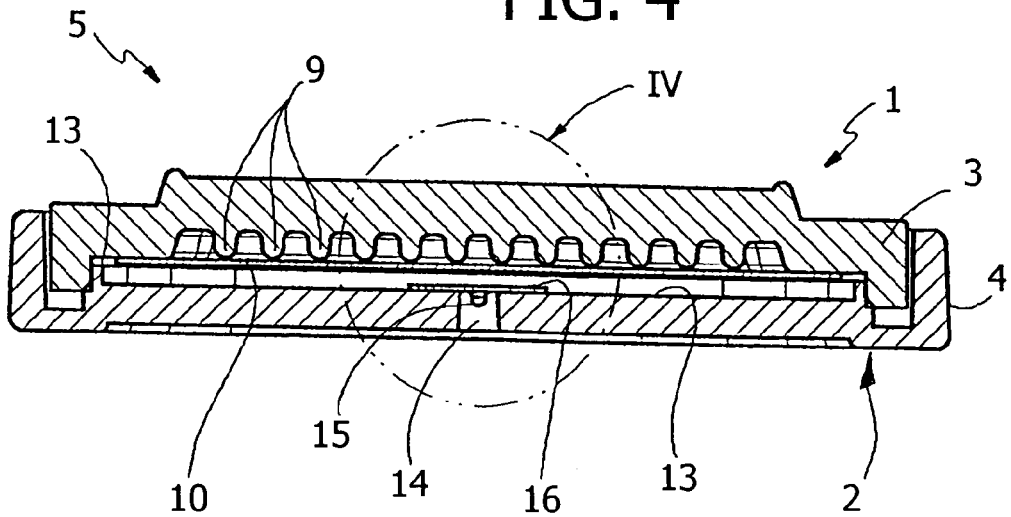

FIG. 2
FIG. 3
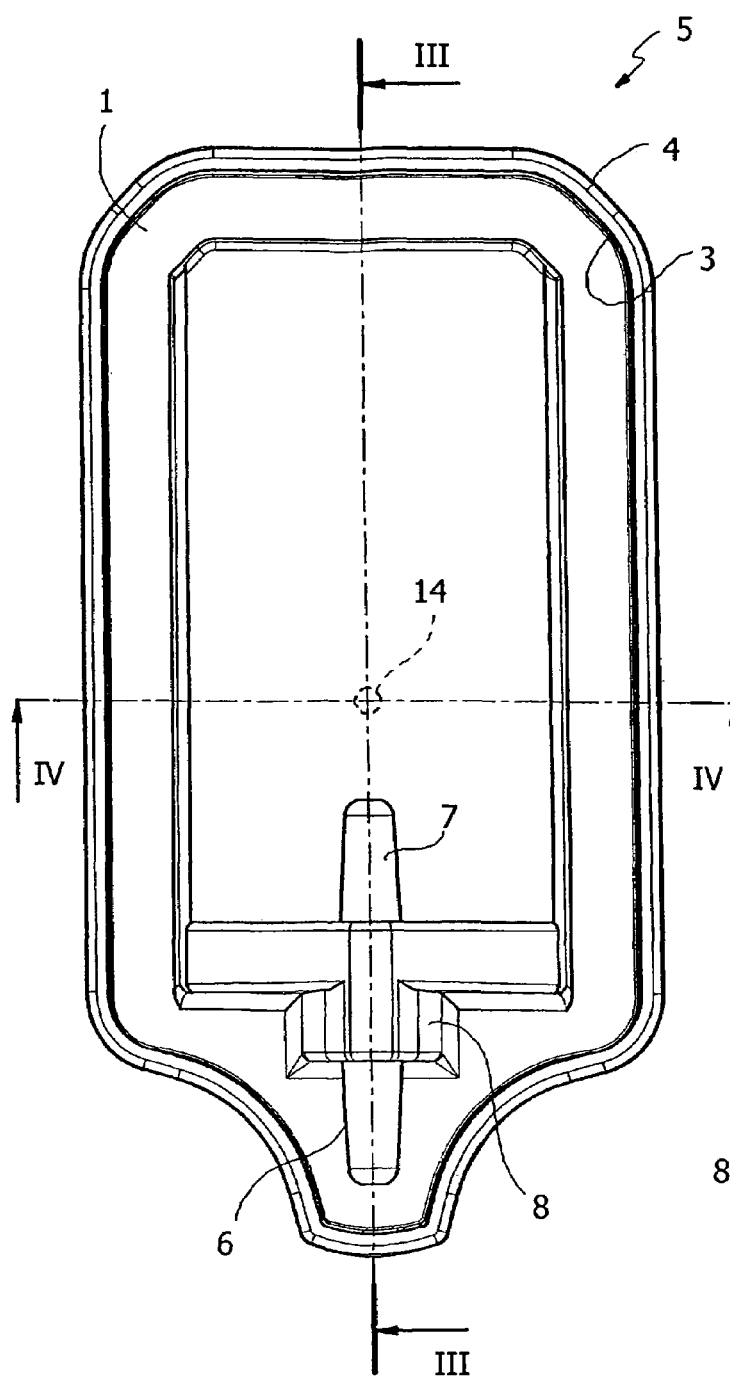
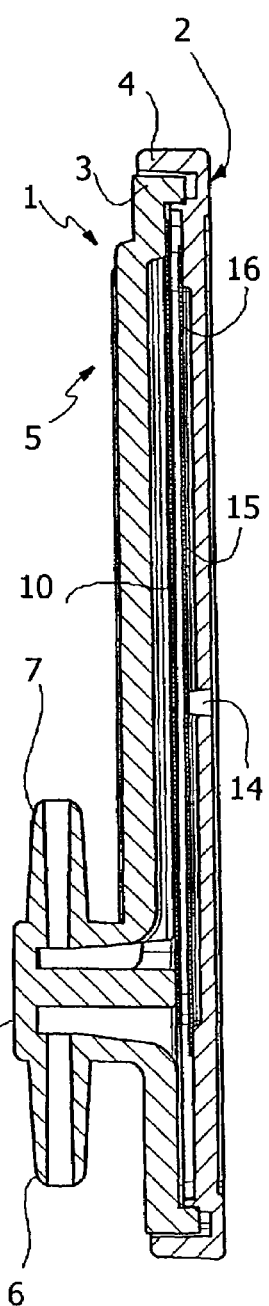

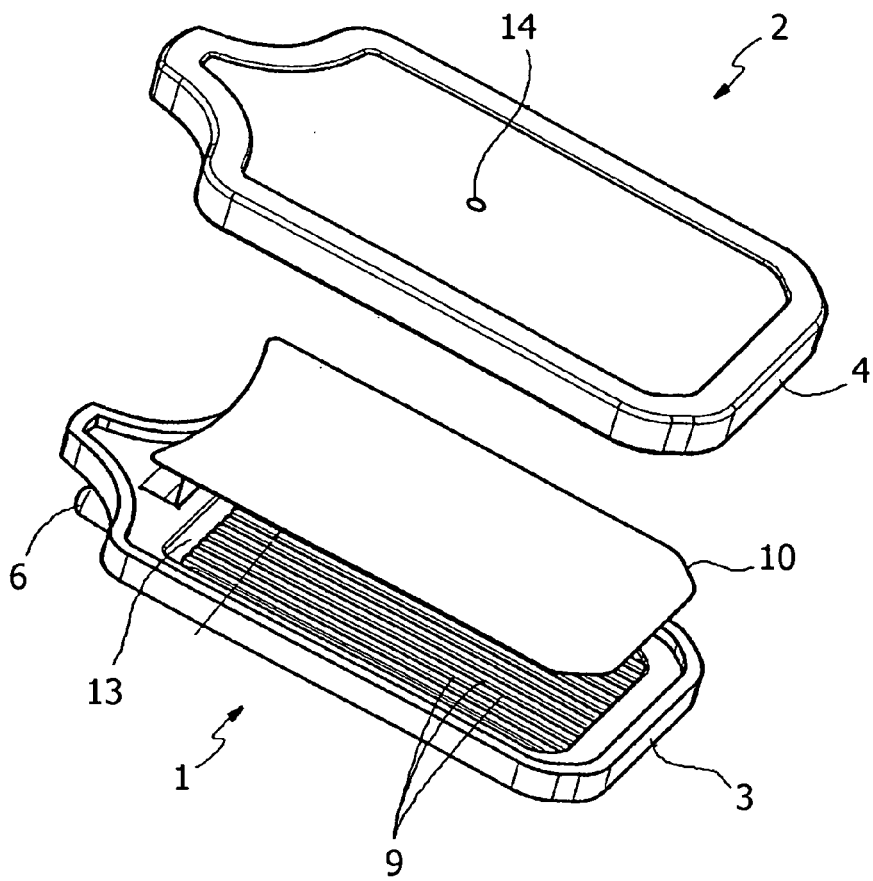
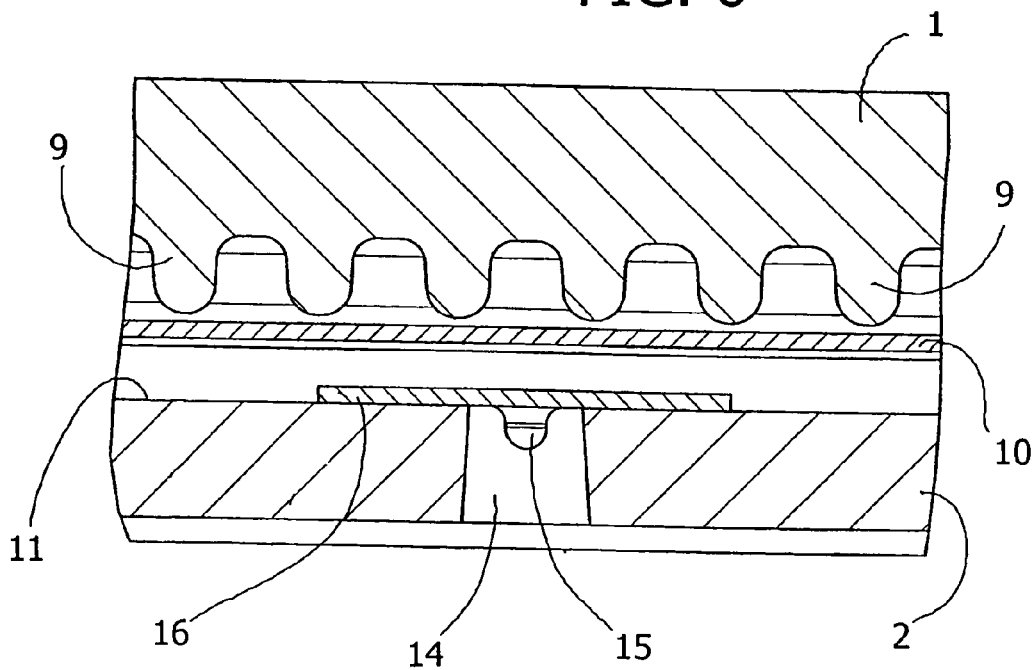

US 6,989,002 B2

FLAT FILTER FOR VENTING GAS IN INTRAVENOUS MEDICAL LINES

FIELD OF THE INVENTION

The present invention relates to a flat filter for venting gas in intravenous medical lines.

More in particular, the invention relates to such a flat filter of the type comprising a case having an inlet and an outlet and formed by a front plate and by a dorsal plate mutually superposed and coupled peripherally in hermetic fashion, a hydrophilic filtering membrane interposed between the two plate and in use traversed by the intravenous fluid entering the case through the inlet and exiting from the case through the outlet, and vent opening means with associated hydrophobic membrane means for the escape of the gas from the case.

STATE OF THE PRIOR ART

Such flat filters are known for example from the documents EP-A-0302722 in the name of Gelman, EP-A-0784988 in the name of Filtertek and EP-A-1214955 in the name of Industrie Borla S.p.A.

In the document EP-A-0302722 the inlet and the outlet are positioned one on the frontal plate and the other one on the dorsal plate of the case, and the vent opening means consist of at least two distanced through holes formed in the frontal plate, and provided with respective hydrophobic membranes.

In the case of the documents EP-A-0784988 and EP-A1214955 the inlet and the outlet are formed in opposite condition in correspondence with a projection situated at an end of the frontal plate, and the vent opening means also consist of a pair at least of through holes with associated hydrophobic membranes provided, in the case of the first document, both on the frontal plate, and in the case of the second document both on the dorsal plate of the case.

In the practical embodiment of such known flat filters the hydrophobic membranes, obviously permeable to gases, have a circular shape with diameter in the order of 10 mm and are obtained starting from a continuous ribbon, whose width is normally 14 mm. The membranes are die cut from the ribbon with the inevitable production of scrap both in the direction of width, and in the direction of the length of the ribbon. By way of indication, with a diameter of 10 mm of the circular membranes, for each pair it is necessary to use about 336 mm$^2$ of ribbon, whose cost is far from negligible. There is also the complication due to the need to dispose of the ribbon scraps.

SUMMARY OF THE INVENTION

The object of the present invention is to overcome the aforesaid drawbacks.

According to the invention, this object is achieved thanks to the fact that a flat filter of the type defined at the beginning is primarily characterised in that the aforesaid vent opening means are constituted by a single through hole of said dorsal plate communicating with an elongated collecting channel formed on the inner wall of said dorsal plate, and in that along and on said collecting channel a hydrophobic membrane is applied having an elongated configuration which is complementary to that of said collecting channel.

Thanks to this solution idea, a considerable saving is obtained on the quantity of hydrophobic membrane used. By way of example, in the case in which the collecting channel extends centrally along the inner wall of the dorsal plate for a substantial length thereof, the membrane may have a rectangular shape with dimensions in the order of 47 mm×6 mm. Such a membrane assures an effective discharge surface area of 86 mm$^2$, with an increase of over 50% with respect to the case of two circular membranes with actual discharge surface area of about 56 mm$^2$. Moreover, said membrane can be obtained from a ribbon whose width is 6 mm without any production of scraps, which means that only 282 mm$^2$ of membrane would then be used for the filter, with savings in the order of 16% and more of material and without any problem with disposing of the scraps.

An additional important advantage of the invention resides in the fact that, thanks to the presence of the collecting channel, in use air is released through the vent hole in continuous fashion, hence more efficiently than in known solutions with two separate holes. Moreover, if the inlet and the outlet of the case are both positioned at an end of the frontal plate, the flat filter according to the invention can advantageously be used positioning the case with said end oriented indifferently either upwards or downwards.

According to a preferred embodiment of the invention the only venting hole is positioned in a substantially median area of the collecting channel, whose cross section can be C shaped, U shaped or have any other geometry.

BRIEF DESCRIPTION OF THE DRAWINGS

The invention shall now be described in detail with reference to the accompanying drawings, provided purely by way of non limiting example, in which:

FIG. 1 is an exploded front perspective view of a flat filter for intravenous medical lines according to the invention, FIG. 2 is an enlarged front elevation view of the flat filter, FIG. 3 is a longitudinal section view according to the line III—III of FIG. 2, FIG. 4 is an enlarged cross section view according to the line IV—IV of FIG. 2, FIG. 5 is a view, similar to FIG. 1, of the dorsal side of the filter, and FIG. 6 is an enlarged view of the detailed indicated by the arrow VI in FIG. 4.

DETAILED DESCRIPTION OF THE INVENTION

With reference to the drawings, a flat filter according to the invention, intended for use in an intravenous medical line, is formed by two superposed plates, respectively front plate 1 and dorsal plate 2, both made of normally transparent plastic material and mutually coupled in hermetic fashion along the respective peripheral edges 3, 4 in the manner shown in detail in FIGS. 2 and 3, for instance by means of ultrasonic welding, gluing or equivalent systems.

The two plates 1 and 2 thus define a case 5 through which the intravenous fluid is made to pass entering from a tubular inlet 6 and exiting from a tubular outlet 7. In the case of the illustrated example, the two tubular conduits 6, 7 project from opposite parts from an integral projection 8 formed at an end of the frontal plate 1, in substantially similar fashion to what is described and illustrated in the aforementioned document EP-A-1214955.

The inner wall 13 of the frontal plate 1 is formed with a series of longitudinal projections 9 against which bears a hydrophilic filtering membrane 10 which faces the inner surface 11 of the dorsal plate 2 and whose peripheral edge is joined to the inner wall 13 of the frontal plate 1, with any suitable system. The projections 9 thereof thus define a plurality of flow channels through which in use the intravenous fluid injected into the case through the inlet 6 is fed and the filtered through the membrane 10, subsequently to return to the line through the outlet 7. To ensure that, during the initial filtering stage, all of the air present inside the case 5 is made to flow outwards, the filter according to the invention is provided with a new and original vent system, comprising a single through hole 14 formed in a substantially central area of the dorsal plate 2, in correspondence with an elongated collecting channel 15 provided on the inner face 11 of said dorsal plate 2. In the case of the illustrated example, the collecting channel 15 has a linear configuration, elongated according to the centreline of the dorsal plate 2 and has, in the manner better visible in FIG. 6, a substantially C shaped section. It should, however, be stressed that the extension, the dimensions, the configuration and the path followed by the collecting channel 15 may differ from the example illustrated in the drawings.

The collecting channel 15 extends longitudinally for a substantial portion of the plate 2 and it is closed in correspondence with the inner surface 11 of said plate by a hydrophobic membrane 16 whose longitudinal extension and transverse extension are such as to allow it to be hermetically fastened, with any suitable system, to the inner wall 11 of the lower plate 2.

In use, the collecting channel 15 allows effectively to collect the air conveyed therein through the hydrophobic membrane 16 upon inserting the intravenous liquid into the filter, subsequently conveying it to the exterior through the sole vent hole 14.

The advantages deriving from the arrangement of the venting system described above have already been illustrated previously: they can be summarised in an appreciable saving on the quantity of hydrophobic membrane to be used, with the elimination of waste due to scraps, and in the fact that in use the escape of air through the vent hole occurs continuously, and hence more efficiently than in prior art solution comprising two separate holes, thanks to the presence of the collecting channel communicating with the single hole. Moreover, with the arrangement illustrated in the example, the flat filter according to the invention can advantageously be used positioning the case with the end bearing the inlet and the outlet conduits oriented indifferently upwards or downwards.

Naturally, the construction details and the embodiments may be widely varied with respect to what is described and illustrated herein, without thereby departing from the scope of the present invention as defined in the claims that follow. Thus, for instance, the collecting channel 15 could be positioned, instead of along the centreline of the case, adjacent to one or the other side or also obliquely.

What is claimed is:

1. A flat filter for venting gas in intravenous medical lines, comprising a case having an inlet and an outlet and formed by a frontal plate and by a dorsal plate peripherally superposed on each other and mutually coupled in hermetic fashion, a hydrophilic filtering membrane interposed between said plates and, in use, traversed by the intravenous fluid entering the case through said inlet and exiting from said case through said outlet, and vent opening means with associated hydrophobic membrane means for the escape of gas from the case, said vent opening means being constituted by a single through hole of said dorsal plate communicating with an elongated collecting channel formed on the inner wall of said dorsal plate, along and on said collecting channel a hydrophobic membrane being applied having an elongated configuration complementary to that of said collecting channel, wherein said collecting channel extends longitudinally substantially along the centerline of said dorsal plate, and wherein said single vent hole is positioned in a substantially median position of said collecting channel.

2. Flat filter as claimed in claim 1, wherein said collecting channel has a linear configuration.

3. Flat filter as claimed in claim 1, wherein said inlet and said outlet are positioned at an end of said frontal plate.

* * * * *